(12) United States Patent
Mallett

(10) Patent No.: US 11,452,462 B2
(45) Date of Patent: Sep. 27, 2022

(54) SPLIT MAGNET WITH ROTATING CENTRAL COMPONENT

(71) Applicant: Siemens Healthcare Limited, Camberley (GB)

(72) Inventor: Michael Mallett, Oxford (GB)

(73) Assignee: Siemens Healthcare Limited, Camberley (GB)

( * ) Notice: Subject to any disclaimer, the term of this patent is extended or adjusted under 35 U.S.C. 154(b) by 297 days.

(21) Appl. No.: 16/811,433

(22) Filed: Mar. 6, 2020

(65) Prior Publication Data

US 2020/0281502 A1 Sep. 10, 2020

(30) Foreign Application Priority Data

Mar. 8, 2019 (GB) .................................. 1903118.6

(51) Int. Cl.
*A61B 5/055* (2006.01)
*G01R 33/36* (2006.01)
*G01R 33/3815* (2006.01)
*G01R 33/385* (2006.01)

(52) U.S. Cl.
CPC .......... *A61B 5/055* (2013.01); *G01R 33/3607* (2013.01); *G01R 33/385* (2013.01); *G01R 33/3815* (2013.01)

(58) Field of Classification Search
CPC ................ A61B 5/055; G01R 33/3607; G01R 33/3815; G01R 33/385
See application file for complete search history.

(56) References Cited

U.S. PATENT DOCUMENTS

| 5,786,694 A | 7/1998 | Kilian et al. |
| 6,466,018 B1 | 10/2002 | Dumoulin et al. |
| 2003/0174036 A1 | 9/2003 | Wang et al. |
| 2011/0199085 A1* | 8/2011 | Allen .................. A61N 5/1071 324/309 |
| 2014/0107468 A1* | 4/2014 | Calvert .............. G01R 33/3815 600/411 |
| 2015/0247907 A1* | 9/2015 | Heid .................... A61B 6/4417 600/411 |
| 2016/0187436 A1 | 6/2016 | Piron et al. |

(Continued)

FOREIGN PATENT DOCUMENTS

| EP | 3047292 A1 | 7/2016 |
| GB | 2549916 A | 11/2017 |

(Continued)

OTHER PUBLICATIONS

United Kingdom Intellectual Property Office Search Report for Great Britain Application No. GB1903118.6, dated Aug. 20, 2019.

(Continued)

*Primary Examiner* — G. M. A Hyder
(74) *Attorney, Agent, or Firm* — Banner & Witcoff Ltd.

(57) ABSTRACT

A Magnetic Resonance Imaging (MRI) system, including: two separate static magnetic field generators, which are each cylindrical, are axially aligned, and are separated by a rotary load-bearing structure arranged to freely rotate about an axis of a static magnetic field generated by the static magnetic field generators, wherein the rotary load-bearing structure is mounted on thrust bearings which take an axial load between the static magnetic field generators.

11 Claims, 5 Drawing Sheets

(56) References Cited

U.S. PATENT DOCUMENTS

2017/0120075 A1* 5/2017 Overweg ............. A61N 5/1081
2019/0274649 A1* 9/2019 Fahrig ................. A61B 6/4417
                                                    600/411

FOREIGN PATENT DOCUMENTS

| GB | 2582009 A | | 9/2020 |
|---|---|---|---|
| KR | 2015033010 A | * | 4/2015 |
| WO | 1998/012964 A1 | | 4/1998 |
| WO | 2011008969 A1 | | 1/2011 |
| WO | 2015/040473 A1 | | 3/2015 |

OTHER PUBLICATIONS

Search Report and Written Opinion dated Oct. 27, 2020 for Netherland Patent No. 2025064.

* cited by examiner

US 11,452,462 B2

SPLIT MAGNET WITH ROTATING CENTRAL COMPONENT

TECHNICAL FIELD

The present disclosure relates to superconducting magnets, in particular to split-pair superconducting magnets for magnetic resonance imaging (MRI) systems combined with radiation therapy equipment and/or equipment for surgical intervention during MRI imaging.

BACKGROUND

A typical split pair superconducting magnet consists of two separate magnet components which have mechanical supports between them to ensure that a magnetic load between them is adequately reacted. Thermal and electrical interconnections are typically provided to ensure continuity of driving current and thermal behaviour. The present disclosure relates to a split pair superconducting magnet that may consist of two magnet components in close proximity with a magnetic force bearing component located between the two magnet components.

FIG. 1 shows a conventional split-pair superconducting magnet arrangement for a combined MRI and radiation therapy system. Two static magnetic field generators 10, such as cryostats, are provided, as illustrated in FIG. 1 in cross-section through magnet axis A-A. Each of the cryostats will contain magnet coils, and between them, the magnet coils will generate static magnetic field in an imaging region centred on the axis A-A and located between the two cryostats. The particular arrangement of magnet coils does not form part of the present disclosure, and so the magnet coils and other contents of the static magnetic field generators 10 are not shown in the drawings. The imaging region centred on the axis A-A and located between the two cryostats corresponds to a treatment region for treatment by radiation therapy equipment and/or equipment for surgical intervention during MRI imaging.

The static magnetic field is typically very strong, with current MRI systems employing magnetic fields of strength in the range 1.5 T-3 T. The two magnetic field generators such as cryostats 10, will experience strong forces of mutual attraction. To retain the cryostats at desired respective positions, mechanical supports 12 are provided. These are mechanically strong and are mechanically attached to the two cryostats 10. According to the magnet design, in terms of the size and layout of respective magnet coils, the mechanical supports may be placed in mechanical compression. Mechanical supports 12 are typically placed intermittently around the cylindrical cryostats, and typically bear forces in a direction parallel to the magnet axis A-A.

In a combined MRI/radiation therapy equipment, it is necessary to provide access to the imaging region in the centre of the magnet arrangement for radiation therapy beams, and maybe also for equipment for surgical intervention such as therapy robots, conventional in themselves. By placing mechanical supports 12 intermittently around the cryostats, access points are provided for radiation therapy beams, and equipment for surgical intervention.

However, drawbacks with such an arrangement include that the presence of mechanical supports 12 mean that certain positions—where the mechanical supports 12 are located—are not available for direction of radiation therapy beams or equipment for surgical intervention. A gantry of some sort must be provided upon which to mount radiation therapy beam equipment or equipment for surgical intervention. This requires a significant structural assembly outside of the cryostats.

Some conventional arrangements have attempted to mitigate these difficulties by limiting an amount of azimuthal access to a patient, to exclude any locations where there is a load bearing support, restricting access for radiation beams or physical access for surgical intervention.

In an attempt to provide full azimuthal access, some conventional systems allow for increased particle beam intensity, to be directed at support elements, such that a sufficient particle beam intensity passes through the support structure to reach the treatment region. This approach, however, must tolerate much higher particle beam intensity, diffraction absorption and scattering of the therapy beam, and in any case does not improve access to a patient for surgical intervention.

In an alternative approach, certain conventional arrangements have provided load bearing structures outside of a volume occupied by the cryostats. Such arrangements provide full access to the patient but require a much larger magnet structure with large load bearing structures at a greater distance from the magnet axis A-A. The complexity and physical size of the system is accordingly increased.

Documents relating to similar topics include EP3047292, U.S. Pat. No. 6,466,018, WO1998/012964, and U.S. Pat. No. 5,786,694.

The present disclosure provides an arrangement which seeks to mitigate these disadvantages, among others.

BRIEF DESCRIPTION OF THE DRAWINGS

The above, and further, objects, characteristics and advantages of the present disclosure will become more apparent from consideration of the following description of certain aspects, given by way of examples only, wherein.

DETAILED DESCRIPTION

The present disclosure provides a rotary load-bearing structure between the two cryostats. The rotary load-bearing structure is mounted on thrust bearings which take the axial magnetic load between the two cryostats. The bearings also serve to accurately locate the rotary load-bearing structure and allow free rotation of the rotary load-bearing structure around the axis A-A of the magnet and the magnetic field. A radiation beam source and/or surgical intervention equipment mounted to the rotary load-bearing structure may be rotated into any circumferential position around the magnet axis A-A to allow access at any angle for surgical intervention equipment or an electromagnetic or particle radiation beam source with no risk of diffraction, absorption or attenuation of the electromagnetic or particle radiation beam. The gantry rotates around the central magnet axis, but the gantry does not move in any radial direction.

Figure 1:
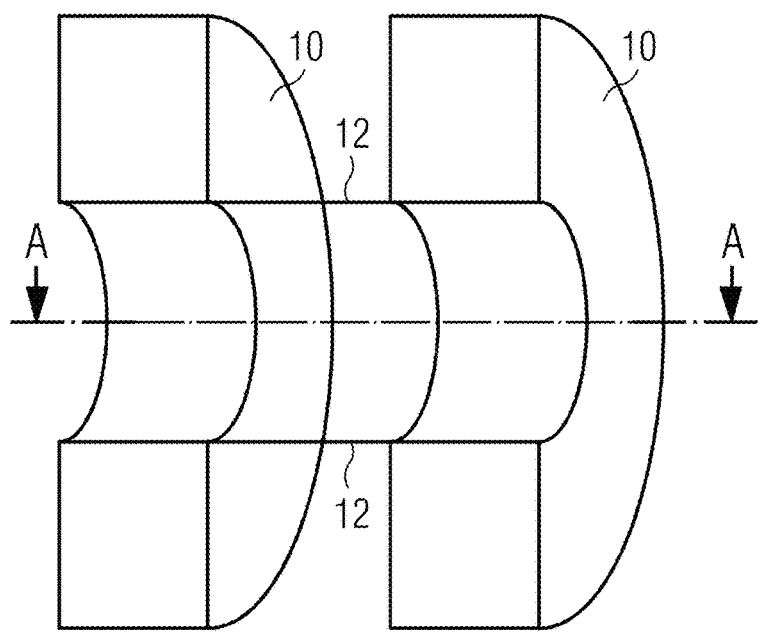
FIG. 1 shows an axial cross-section through a conventional split-pair superconducting magnet arrangement for a combined MRI and radiation therapy system.
Figure 2:
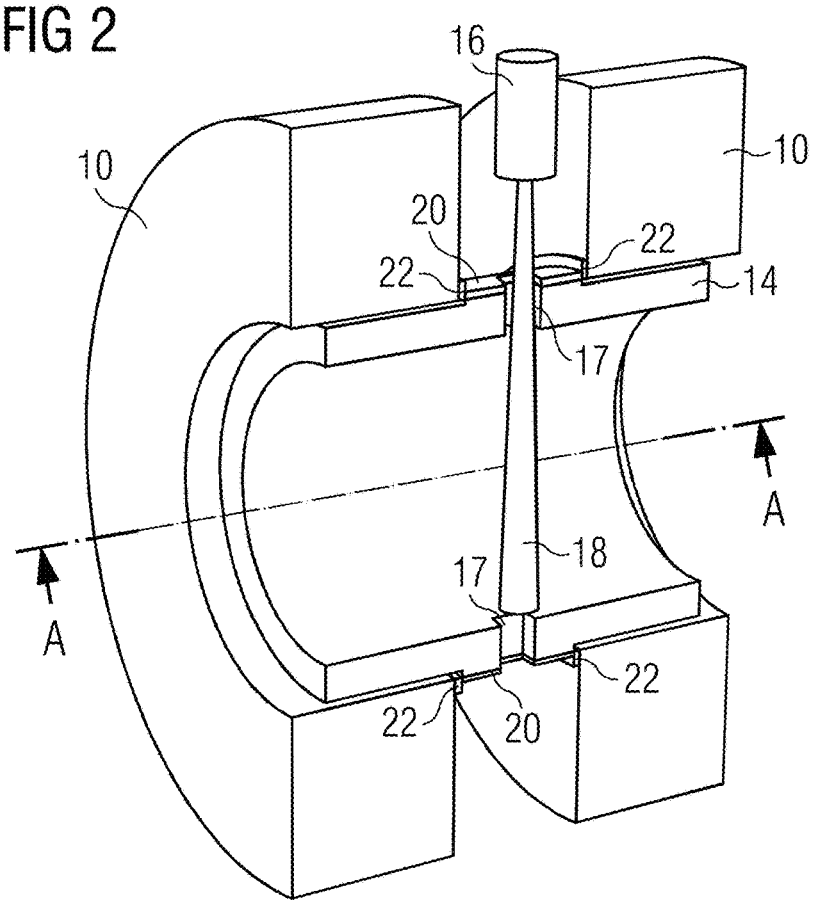
FIG. 2 shows an axial cross-section through a combined MRI and radiation therapy equipment according to a first aspect of the present disclosure.

An aspect of the present disclosure is illustrated in FIG. 2. As described in relation to FIG. 1, two cryostats are provided, spaced apart. However, instead of being axially restrained in required relative positions against axial magnetic forces by mechanical supports 12, the two cryostats 10 in the aspect of FIG. 2 are axially restrained by a rotary load-bearing structure 20 mounted on thrust bearings 22.

The rotary load-bearing structure 20 can be freely rotated independent of the two cryostats 10, around the axis A-A of the static magnetic field.

In the illustrated aspect, the thrust bearings 22 are located at axially and radially inner edges of respective cryostats 10. In the illustrated aspect, the rotary load-bearing structure 20 extends between the thrust bearings 22. The rotary load-bearing structure, in this aspect, is axially aligned with the magnet structure and rotates about the magnet axis A-A. Also illustrated in FIG. 2 are a radiation beam source 16 and a gradient coil assembly 14. The radiation beam source 16 is mounted to the rotary load-bearing structure 20 and is able to rotate about magnet axis A-A with the rotary load-bearing structure 20.

In the illustrated aspect, the gradient coil assembly 14 comprises two apertures 17 aligned with radiation beam 18 generated by radiation beam source 14. Corresponding apertures are provided in the rotary load-bearing structure 20 to provide an unimpeded path for the radiation beam 18 through the imaging region, which is coincident with the treatment region. In the illustrated aspect, the gradient coil assembly 14 is also arranged to rotate with the rotary load-bearing structure 20. The radiation beam source 16 may accordingly rotate about axis A-A while maintaining alignment of the radiation beam 18 with apertures 17. Gradient coil assembly 14 may be mounted to the rotary load-bearing structure, in turn mounted to the thrust bearings 22; or gradient coil assembly 14 may be mounted on a separate set of bearings (not illustrated in FIG. 2) and may be controlled to rotate in synchronisation with rotary load-bearing structure 20. In another aspect, rotary load-bearing structure 20 and gradient coil assembly 14 may be separately controlled, but a user must then ensure that apertures on the rotary load-bearing structure 20 and in the gradient coil assembly 14 both align with radiation beam 18 before the radiation beam is brought into use. Thrust bearings 22 and rotary load-bearing structure 20 bear the compressive magnetic force between the two cryostats 10.

Figure 8:
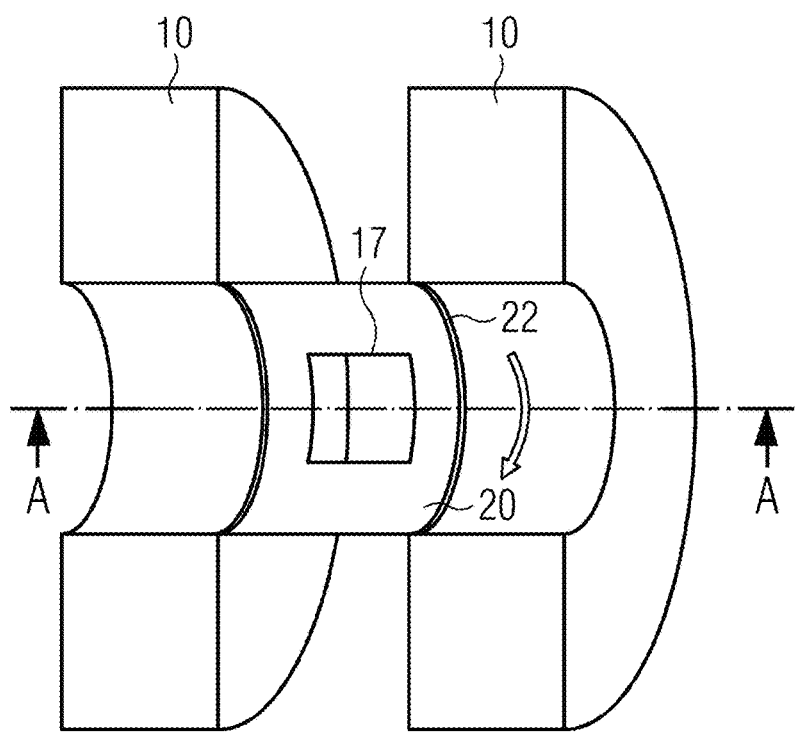
FIG. 8 schematically represents an aspect of the present disclosure.

As schematically represented in FIG. 8, the rotating central component will typically consist of a tube-like cylindrical structure with a thrust bearing 22 on either end where it connects to the magnetic field generators 10. The tube-like cylindrical structure 20 will typically have one or more aperture 17 near the centreline to allow unimpeded access for a particle beam. The use of such apertures in the tube-like structure 20 ensures no degradation, reflection or modulation of a particle beam will occur, or that free access to the treatment region is available for other devices, for example, a robot therapy device.

To ensure that there is full circumferential access to the imaging region, the gradient coil assembly 14 and any RF body coil (not shown in the drawings) may preferably also be mounted to the rotary load-bearing structure 20 and rotate with it. Any such RF body coil may have a similar aperture 17 near its centreline to ensure no impediment to physical or particle beam access to the treatment region. Each aperture should be transparent to the radiation beam 18. If surgical intervention equipment is provided, the apertures 17 should allow physical access to the treatment region.

Figure 3:
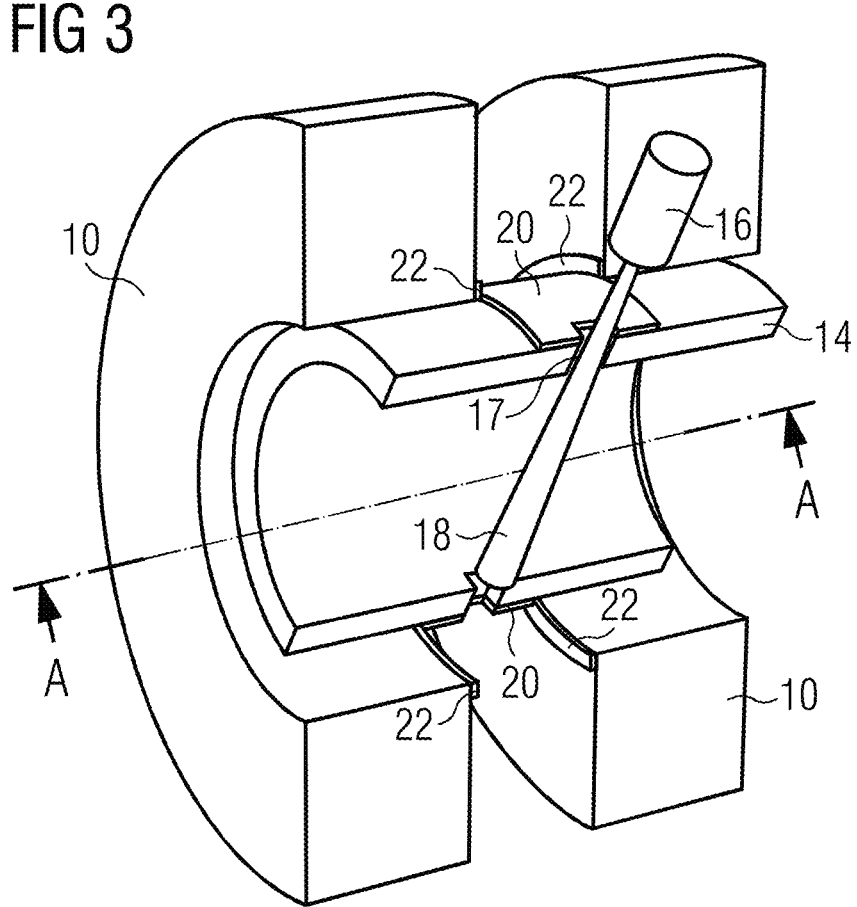
FIG. 3 illustrates the arrangement of FIG. 2 in use, in a configuration displaced from the configuration of FIG. 2.

FIG. 3 illustrates the aspect of FIG. 2 in which the rotary load-bearing structure 20, the radiation beam source 16 and the gradient coil assembly 14 have been rotated about the A-A axis by approximately 30°. Although only one half of the cryostats 10, the rotary load-bearing structure 20 and the gradient coil assembly 14 are shown in FIG. 3, this is for illustration purposes only. The half components shown in FIG. 3 are the halves shown in FIG. 2, by way of illustration of the rotation imparted to some of the components. Of course, in reality, rotary load-bearing structure 20, gradient coil assembly 14 and cryostats 10 are fully cylindrical. In the aspect of FIG. 3, the gradient coil assembly 14 is mounted to the rotary load-bearing structure 20 and is not provided with its own bearings.

The thrust bearings 22 allow free rotation of the rotary load-bearing structure 20. The bearings 22 can be roller bearings, ball bearings, plain bearings or any other form of bearing that can react the magnetic load and ensure accurate positioning of the cryostats 10 and the rotary load-bearing structure 20 with respect to each other. The thrust bearings 22 are preferably axisymmetric in nature about axis A-A, so any ferrous components within the bearings 22 provide an axisymmetric effect on the magnetic field and can therefore be relatively simply cancelled by appropriate shimming.

The bearings 22 may also react the full vertical weight load of the gradient coil, body coil and other components connected to the rotary load-bearing structure 20. In alternative aspects, there may be a separate bearing component to react these vertical weight loads.

Figure 4:
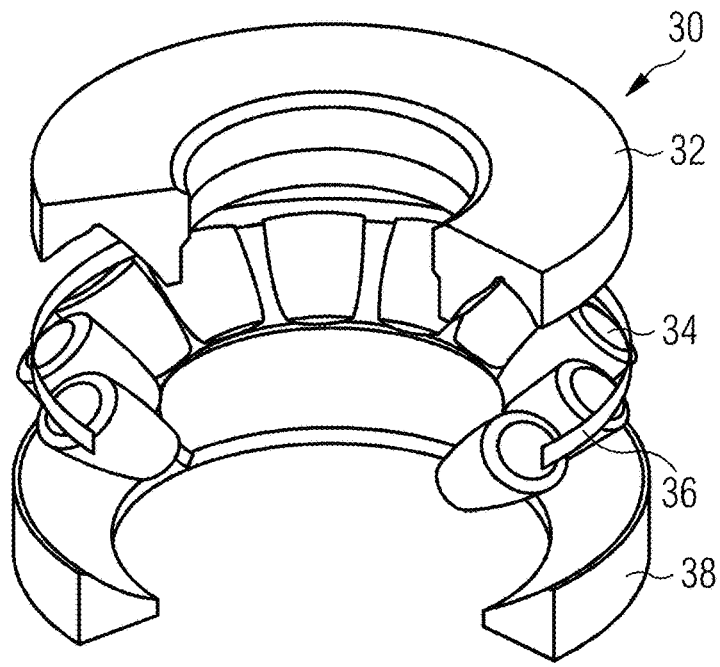
FIGS. 4 and 5 show example types of bearing which may be employed in aspects of the present disclosure.
Figure 5:
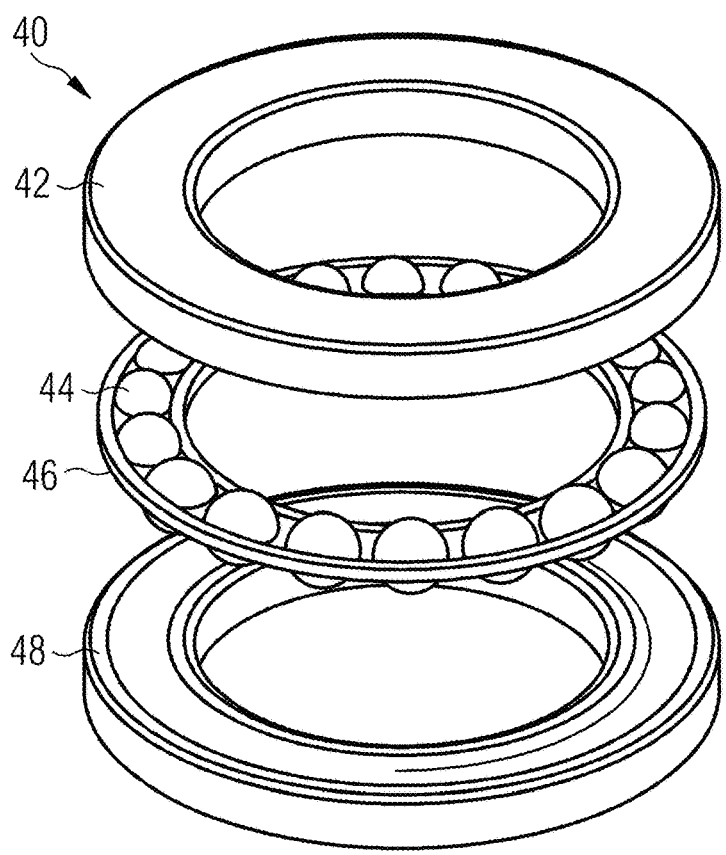

FIGS. 4 and 5 show two types of bearing which may be used as thrust bearings 22 in aspects of the present disclosure. Both types of thrust bearing are conventional in themselves.

FIG. 4 schematically shows, in cut-away, an example of a roller bearing 30 which may be used as thrust bearing 22 in an aspect of the present disclosure. The roller bearing 30 comprises a first washer 32, having an axially outer surface profiled to interface with a surface of a first one of the cryostats 10 and a radially inner surface profiled to interface with rolling elements 34; rolling elements 34 in the form of rollers retained within a cage 36; and a second washer 38, having an axially outer surface profiled to interface with a surface of a second one of the cryostats 10 and a radially inner surface profiled to interface with the rolling elements 34. A suitable grease may be applied to the rolling elements 34.

FIG. 5 schematically shows, in cut-away, an example of a ball bearing 40 which may be used as bearing 22 in an aspect of the present disclosure. The ball bearing 40 comprises a first washer 42, having an axially outer surface profiled to interface with a surface of a first one of the cryostats 10 and a radially inner surface profiled to interface with rolling elements 44; rolling elements 44 in the form of balls retained within a cage 46; and a second washer 48, having an axially outer surface profiled to interface with a surface of a second one of the cryostats 10 and a radially inner surface profiled to interface with the rolling elements 44. A suitable grease may be applied to the rolling elements 44.

The thrust bearings 22 should provide consistent, reproducible behaviour in the axial direction to ensure repeatable magnetic homogeneity of the static magnetic field. The thrust bearings 22 should provide repeatable behaviour under a static load case but need not necessarily provide such repeatable behaviour during dynamic rotation as MR imaging is likely to be performed only while the rotary load-bearing structure 20 is static. If MR measurements are required during dynamic rotation of the rotary load-bearing structure 20, the thrust bearings 22 should also provide repeatable behaviour under these conditions as well.

The typical level of bearing repeatable accuracy in the axial direction must be sufficient to cope with a typical 100 PPM/mm level of field variation for axial separation movement of the two cryostats 10. The operating load case is with the thrust bearings 22 under constant magnetic axial load. This loading should be beneficial to eliminate any float in the bearings and to take up any clearances from an uncompressed state of the bearings.

Figure 6:
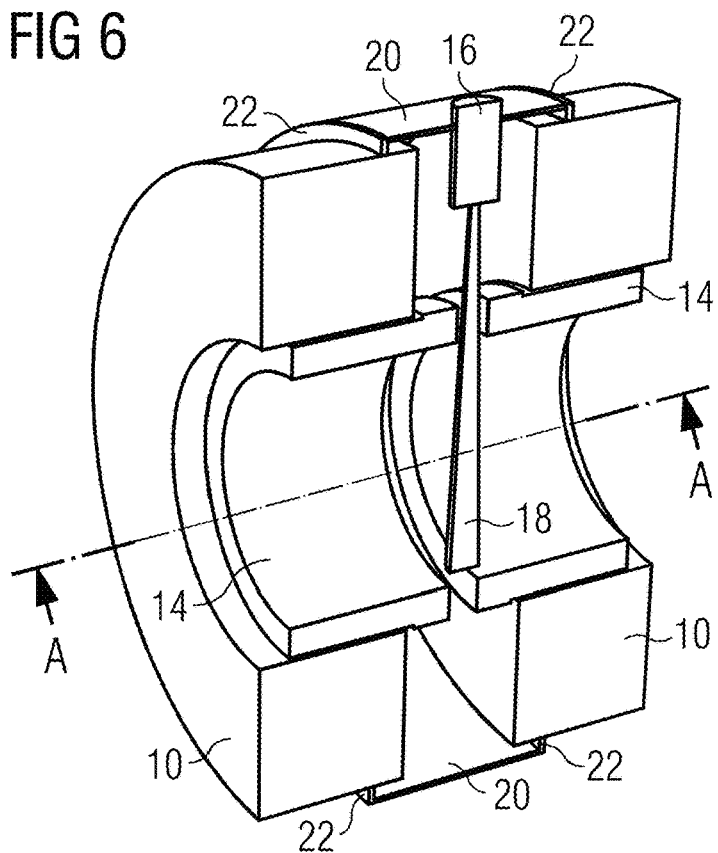
FIG. 6 shows an axial cross-section through a combined MRI and radiation therapy equipment according to a second aspect of the present disclosure.

Another aspect of the present disclosure is illustrated in FIG. 6. As described in relation to FIG. 1, two cryostats 10 are provided, spaced apart. However, instead of being held in required relative positions by mechanical supports 12, the two cryostats 10 in the aspect of FIG. 6 are held apart by a rotary load-bearing structure 20 mounted on bearings 22. In this aspect, the bearings 22 are located at axially inner and radially outer edges of respective cryostats 10. The rotary load-bearing structure 20 extends between the bearings. The rotary load-bearing structure 20, in this aspect, is axially aligned with the magnet structure and rotates about the magnet axis A-A.

Also illustrated in FIG. 6 are a radiation beam source 16 and a gradient coil assembly 54. Gradient coil assembly 54 is provided in two parts, one part mounted to each of the two cryostats 10. A gap 56 is provided between the two parts of the gradient coil assembly 54, to provide access for the radiation beam 18 to the imaging region, which is coincident with the treatment region.

The radiation beam source 16 is mounted to the rotary load-bearing structure 20, and is able to rotate about magnet axis A-A with the rotary load-bearing structure 20. In this aspect, radiation beam source 16 is mounted to the rotary load-bearing structure 20 and generates a radiation beam 18 inside of the rotary load-bearing structure 20. As the radiation beam 18 is generated inside of the rotary load-bearing structure, the rotary load-bearing structure 20 does not impede the radiation beam 18 from reaching the treatment region. As discussed above, the gradient coil assembly is provided as two parts 54, with a gap 56 between. The radiation beam is therefore able to pass through the gap 56 and is not impeded by the gradient coil assembly.

The radiation beam source 16 may accordingly rotate about axis A-A while maintaining access of the radiation beam 18 to the radiation treatment volume. Thrust bearings 22 and rotary load-bearing structure 20 bear the compressive force between the two cryostats 10.

Figure 7:
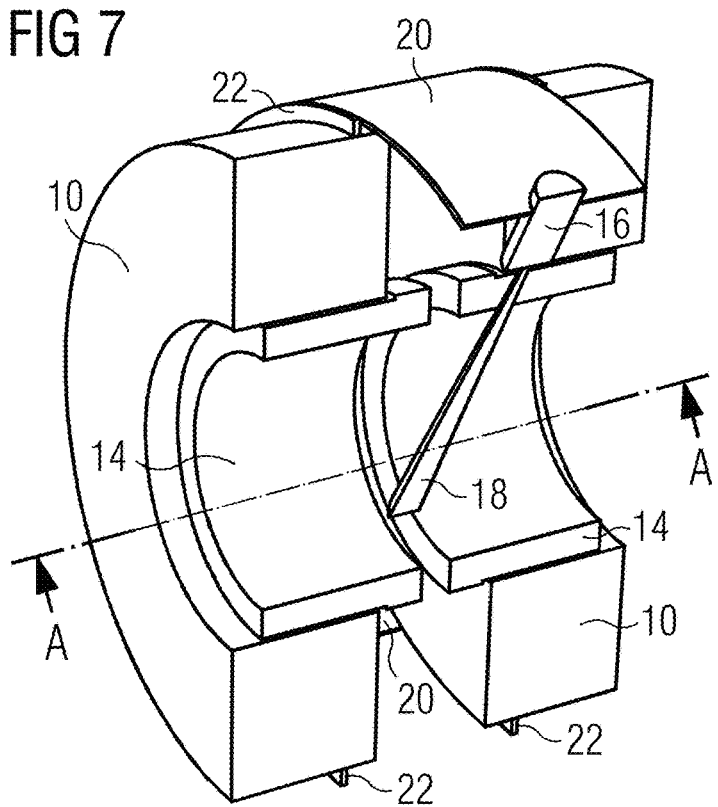
FIG. 7 illustrates the components of FIG. 6 in use, in a configuration displaced from the configuration of FIG. 6.

FIG. 7 illustrates the aspect of FIG. 6 in which the rotary load-bearing structure 20 and the radiation beam source 16 have been rotated about the A-A axis by approximately 30°. Although only one half of the cryostats 10, the rotary load-bearing structure 20 and the gradient coil assembly 14 are shown in FIG. 3, this is for illustration purposes only. The half components shown in FIG. 3 are the halves shown in FIG. 2, by way of illustration of the rotation imparted to some of the components. Of course, in reality, rotary load-bearing structure 20, gradient coil assembly 14 and cryostats 10 are fully cylindrical. In the aspect of FIG. 7, the gradient coil assembly 14 is mounted to the cryostats 10 and is not required to rotate.

In certain aspects of the present disclosure, various objects may be mounted to rotary load-bearing structure 20, which allows the objects to be rotated around the axis A-A of the magnetic field. Examples of such objects which may usefully be mounted in this way include, but are not limited to, linear particle accelerators, angiography devices, therapy robots.

Figure 9:
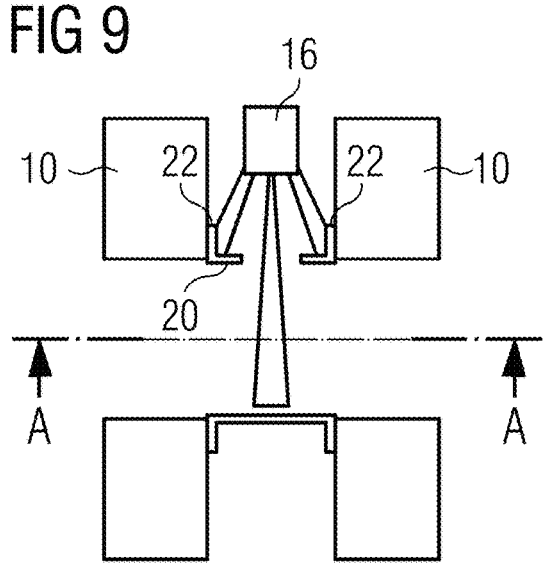
FIG. 9 schematically represents an aspect of the present disclosure comprising a radiation beam source.

FIG. 9 schematically represents an example of an aspect in which a radiation beam source 16 is mounted to rotate with the rotary load-bearing structure 20. As illustrated, the radiation beam source 16 may be mounted to the rotary load-bearing structure 20 itself or may be directly mounted to the thrust bearings 22.

Figure 10:
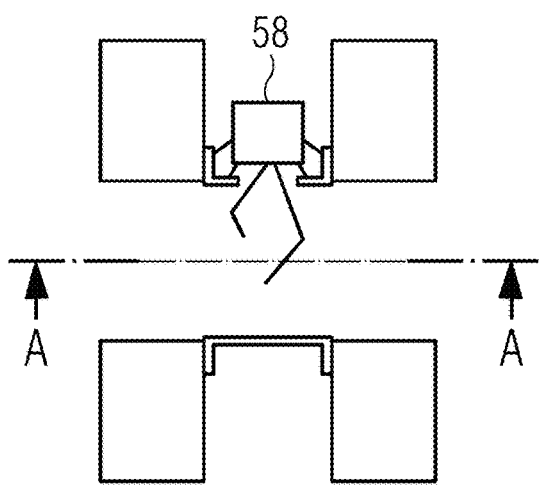
FIG. 10 schematically represents an aspect of the present disclosure comprising a therapy robot.

FIG. 10 schematically represents an example of an aspect in which a therapy robot 58 is mounted to rotate with the rotary load-bearing structure 20. As illustrated, the therapy robot 58 may be mounted to the rotary load-bearing structure 20 itself or may be directly mounted to the thrust bearings 22. In other aspects (not illustrated) a therapy robot may be provided in addition to a radiation beam source, such that both are mounted to a rotary load-bearing structure 20. Provision may be made for the therapy robot and the radiation beam source to rotate independently about the A-A axis.

While the present disclosure has been described with reference to a limited number of particular aspects, given by way of non-limiting examples only, it will be apparent to those skilled in the art that the disclosure may be implemented with numerous variations on the particular aspects described above.

While the above examples have illustrated the rotary load-bearing structure 20 as a thin-walled cylinder, it may take other forms such as a squirrel-cage, provided that it enables the function of mechanically restraining the cryostats 10 against axial magnetic forces and the mounting of equipment such as therapy beam sources, linear particle accelerators, angiography devices, therapy robots.

The thrust bearings 22 can for example be roller bearings, ball bearings, plain bearing, oil bearings or any other type of thrust bearing that provides accurate location of the two magnet units and the rotary load-bearing structure 20 with respect to each other.

The present disclosure accordingly provides a Magnetic Resonance Imaging (MRI) system, comprising two separate static magnetic field generators which are each cylindrical and are axially aligned, and are separated by a rotary load-bearing structure arranged to freely rotate about an axis of a static magnetic field generated by the static magnetic field generators, the rotary load-bearing structure being mounted on thrust bearings which take an axial load between the static magnetic field generators.

Various modifications and variations of the present disclosure will be apparent to those skilled in the art, within the scope of the present disclosure as defined in the appended claims.

The invention claimed is:

1. A Magnetic Resonance Imaging (MRI) system, comprising:
   two separate static magnetic field generators, which are each cylindrical, are axially aligned, and are separated by a rotary load-bearing structure arranged to freely rotate about an axis of a static magnetic field generated by the static magnetic field generators, wherein the rotary load-bearing structure is mounted on thrust bearings which take an axial load between the static magnetic field generators.

2. An MRI system according to claim 1, further comprising:
a radiation beam source mounted to the rotary load-bearing structure such that the radiation beam source is rotatable about the axis with the rotary load-bearing structure.

3. An MRI system according to claim 1, further comprising:
surgical intervention equipment mounted to the rotary load-bearing structure such that the surgical intervention equipment is rotatable about the axis with the rotary load-bearing structure.

4. An MRI system according to claim 1, wherein the two separate static magnetic field generators define an imaging volume axially between and axially aligned with the two separate static magnetic field generators.

5. An MRI system according to claim 4, further comprising:
a cylindrical gradient coil assembly axially aligned with the rotary load-bearing structure and the static magnetic field generators, and located within a bore of the static magnetic field generators.

6. An MRI system according to claim 5, wherein the gradient coil assembly axially extends into the bore of both of the static magnetic field generators and has apertures axially between the static magnetic field generators to provide access to the imaging volume.

7. An MRI system according to claim 5, wherein the gradient coil assembly is provided in two parts, separated axially such that one part respectively extends into the bore of one of the static magnetic field generators.

8. An MRI system according to claim 5, wherein the gradient coil assembly is mounted on bearings other than the thrust bearings.

9. An MRI system according to claim 1, further comprising:
an RF body coil mounted to, and arranged to rotate with, the rotary load-bearing structure.

10. An MRI system according to claim 9, wherein the RF body coil has apertures axially between the static magnetic field generators to provide access to the imaging volume.

11. An MRI system according to claim 1, further comprising:
a further bearing component arranged to react vertical weight loads of the rotary load-bearing structure.

* * * * *